(12) United States Patent
McLaughlin et al.

(10) Patent No.: US 6,783,940 B2
(45) Date of Patent: Aug. 31, 2004

(54) METHOD OF REDUCING NON-SPECIFIC AMPLIFICATION IN PCR

(75) Inventors: Ian J. McLaughlin, Moss Beach, CA (US); Sulekha Rao Coticone, Half Moon Bay, CA (US); Will Bloch, White Salmon, WA (US)

(73) Assignee: Applera Corporation, Foster City, CA (US)

( * ) Notice: Subject to any disclaimer, the term of this patent is extended or adjusted under 35 U.S.C. 154(b) by 55 days.

(21) Appl. No.: 09/998,887

(22) Filed: Oct. 31, 2001

(65) Prior Publication Data

US 2003/0104395 A1 Jun. 5, 2003

(51) Int. Cl.[7] .......................... C12Q 1/68; C12P 19/34; C07H 21/02; C07H 21/04; C07H 19/00

(52) U.S. Cl. ...................... 435/6; 435/7.1; 435/91.1; 435/91.2; 536/22.1; 536/23.1; 536/24.3; 536/24.31; 536/24.32; 536/24.33

(58) Field of Search ................ 435/6, 7.1, 91.1, 435/91.2; 330/22.1, 23.1, 24.3–24.8

(56) References Cited

U.S. PATENT DOCUMENTS

| | | | | |
|---|---|---|---|---|
| 5,364,759 A | | 11/1994 | Caskey et al. ............... | 435/6 |
| 5,545,539 A | | 8/1996 | Miller ....................... | 435/91.2 |
| 5,571,674 A | * | 11/1996 | Hoshina et al. .............. | 435/6 |
| 5,580,728 A | | 12/1996 | Perlin ........................ | 435/6 |
| 5,606,045 A | * | 2/1997 | Dandliker et al. ........ | 536/25.32 |
| 5,846,716 A | | 12/1998 | Miller ....................... | 435/6 |
| 6,077,664 A | * | 6/2000 | Slater et al. ................ | 435/6 |
| 6,156,512 A | | 12/2000 | Schumm et al. ............ | 435/6 |

FOREIGN PATENT DOCUMENTS

| | | |
|---|---|---|
| DE | 44 11 588 C1 | 9/1995 |
| WO | WO 99/46400 | 9/1999 |

OTHER PUBLICATIONS

Atha, D.H. et al., "Detection of p53 point mutations by single strand conformation polymorphism: Analysis by capillary electrophoresis," *Electrophoresis*, 1998, 19, 172–179.

Baskaran, N. et al., "Uniform amplification of a mixture of deoxyribonucleic acids with varying GC content," *Genome Research*, 1996, 6, 633–638.

Bradshaw, P.S. et al., "Fluorescent BAT–25 and BAT–26 analysis of T cell prolymphocytic leukaemia," *BTS Leukemia*, 1999, 13, 2104–2106.

Bruford et al., "Microsatellites and their application to population genetic studies," *Curr Biol*, 1993, 3, 939–943.

Bruland, O. et al., "Accurate determination of the number of CAG repeats in the Huntington disease gene using a sequence–specific internal DNA standard," *Clin Genet*, 1995, 55(3), 198–202.

(List continued on next page.)

*Primary Examiner*—Jeffrey Siew
(74) *Attorney, Agent, or Firm*—Scott R. Bortner; Andrew K. Finn

(57) ABSTRACT

The invention provides methods for reducing non-specific amplification DNA in a polymerase chain reaction comprising providing a sample comprising a target DNA sequence of interest; contacting the sample with at least one enzyme having nucleic acid polymerase activity; and incubating the sample with said enzyme for a time and under conditions sufficient to amplify the target DNA sequence, forming amplified target sequence; wherein the incubation is performed in the presence of an amount of sorbitol, or sorbitol and DMSO effective to reduce the non-specific amplification relative to the amount of non-specific amplification observed in the absence of sorbitol, or sorbitol and DMSO. The methods are suitable for amplification of ribosomal DNA, particularly from clinical samples. Compositions and kits containing sorbitol, or sorbitol and DMSO for reducing non-specific amplification are also provided.

55 Claims, 5 Drawing Sheets

OTHER PUBLICATIONS

Chen et al. "Presence and instability of repetitive elements in sequences the altered expression of which characterizes risk for colonic cancer," *Cancer Res.,* 1995, 55, 174–180.

Chevet, E. et al., "Low concentrations of tetramethylammonium chloride increase yield and specificity of PCR," *Nucl. Acids Res.,* 1995, 23(16), 3343–3344.

Christensen, M. et al., "Comparasion of three methods of microsatellite detection," *Scand J Clin Lab Invest,* 1999, 59 (3), 167–178.

Clark, J.M., "Novel non–templated nucleotide addition reactions catalyzed by procaryotic and eucaryotic DNA polymerases," *Nucleic Acid Research,* 1988, 16, 9677–9686.

Colburn, N.H. et al., "PCR–direct sequencing of GC–rich region by inclusion of 10% DMSO: application to mouse c–jun," *Biotechniques,* 1993, 15(3), 372 and 374.

de la Chapelle, "Testing tumors for microsatellite instability," *Eur. J. Hum. Genet.,* 1999, 7, 407–408.

Del Vecchio, P. et al., "The effects of polyols on the thermal stability of calf thymus DNA," *Int'l Jrnl of Biol Macro,* 1999, 24, 361–369.

Dimo–Simonin, N. et al., "Forensic validation of the short tandem repeat HUMACTBP2 using capillary electrophoresis," *Electrophoresis,* 1988, 19(2), 256–61.

Edwards, A. et al., "DNA typing and genetic mapping with trimeric and tetrameric tandem repeats," *Am J. Hum. Genet,* 1991, 49, 746–756.

Edwards, A. et al., "Genetic Variation a five trimeric and tetrameric tandem repeat loci in four human population groups," *Genomics,* 1992, 12, 241–253.

Eichler, E.E. et al., "Length of uninterrupted CGG repeats determines instability in the FMR1 gene," *Nat Genet,* 1994, 8, 88–94.

Eichler, E.E., et al., "Haplotype and interspersion analysis of the FMR1 CGG repeat identifies two different mutational pathways for the origin of the fragile X syndrome," *Hum Mol Genet,* 1996, 5(3), 319–330.

Frackman S. et al., "Betaine and DMSO: Enhancing agents for PCR," *Promega Notes, 65,* 27–29.

Frazier, R.R.E. et al., "Validation of the applied biosystems, Prism™ 377 automated sequencer for forensic short tandem repeat analysis," *Electrophoresis,* 1996, 17(10), 1550–2.

Frégeau, C. et al., "DNA typing with fluorescently tagged short tandem repeats: A sensitive and accurate approach to human identification," *Biotechniques,* 1993, 15(1), 100–119.

Fujigasaki, H. et al., "SCA12 is a Rare Locus for Autosomal Dominant Cerebellar Ataxia: a Study of an Indian Family," *Ann Neurol,* 2001, 49 (1), 117–21.

Goldstein, D.B. et al., "Genetic absolute dating based on microsatellites and the origin of modern humans," *Proc Natl Acad Sci USA,* 1995, 92, 6723–6727.

Hagelberg, E. et al., "Identification of the skeletal remains of a murder victim by DNA analysis," *Nature,* 1991, 352, 427–429.

Hammond, H. et al., "Evaluation of 13 short tandem repeat loci for use in personal identification applications," *Am J Hum Genet,* 1994, 55, 175–189.

Hauge, X.Y. et al., "A Study of the origin of "shadow bands" seen when typing dinucleotide repeat polymorphisms by the PCR," *Human Molecular Genetics,* 1993, 2(4), 411–415.

Henke, W. et al., "Betaine improves the PCR amplification of GC–rich DNA Sequences," *Nucleic Acids Research,* 1997, 25(19), 3957–3958.

Hengen, P.N. "Optimizing multiplex and LA–PCR with betaine," *TIBS,* 1997, 22, 225 and 226.

Hite, J.M. et al., "Factors affecting fidelity of DNA synthesis during PCR amplification of $d(C-A)_n$ $d(G-T)_n$ microsatellite repeats," *Nucleic Acids Research* 1996, 24(12), 2429–2434.

Ionov, Y. et al., "Ubiquitous somatic mutations in simple repeated sequences reveal a new mechanism for colonic carcinogenesis," *Nature,* 1993, 363, 558–561.

Khidiiatova IM et al., "A Study of Expansion and mutation rate of the CTG Repeat in the myotonic dystrophy gene," *Genetika,* 2000, 36(10), 1410–1413 (English Abstract Provided).

Kovárová, M. et al., "New Specificity and yield enhancer of polymerase chain reactions," *Nucl. Acids Res.,* 2000, 28(13):e70.

Levinson, G. et al., "Slipped–strand mispairing: A Major mechanism for DNA sequence evolution," *Mol. Biol.Evol,* 1987, 4(3), 203–221.

LeProust, E.M. et al., "Unexpected Formation of Parallel Duplex in GAA and TTC Trinucleotide Repeats of Friedreich's Ataxia," *J Mol Biol,* 2000, 302(5), 1063–80.

Lin, T–Y. et al., "Why Do Some Organisms Use a Urea–methylamine Mixtures as Osmolyte? Thermodynamic Compensation of Urea and Trimethylamine N–Oxide Interactions with Protein," *Biochemistry,* 1994, 33, 12695–12701.

Litt, M. et al. "Shadow Bands Seen When Typing Polymorphic Dinucleotide Repeats: Some Causes and Cures," *BioTechniques,* 1993, 15(2), 281–284.

Magnuson, V.L. et al., "Substrate nucleotide– determined non–templated addition of adenine by Taq DNA polymerase: Implications for PCR–based genotyping and cloning," *Biotechniques,* 1996, 21(4), 700–709.

McDowell, D.G. et al., "Localised sequence regions possessing high melting temperatures prevent the amplification of a DNA mimic in competitive PCR," *Nucl. Acids Res.,* 1998, 26(14), 3340–3347.

Müller, T. et al., "GCG repeats and phenotpye in oculopharyngeal muscular dystrophy," *Muscle & Nerve,* 2001, 24(1), 120–2.

Murray, V. et al., "The determination of the sequences present in the shadow bands of a dinucleotide repeat PCR," *Nucleic Acids Research,* 1993, 21(10), 2395–2398.

Mytelka, D.S. et al., "Analysis and suppresion of DNA polymerase pauses associated with a trinucleotide consensus," *Nucleic Acids Research,* 1996, 24(14), 2774–2781.

Notomi, T. et al., "Loop–mediated isothermal amplification of DNA," *Nucl. Acids Res.,* 2000, 28(12):63e.

Odelberg, S.J. et al., "A method for accurate amplification of polymorphic CA–repeat sequences," *PCR Methods and Applications,* 1993, 7–12.

Orosz, J.M. et al., "DNA melting temperatures and renaturation rates in concentrated alkylammonium salt solutions," *Biopolymers,* 1977, 16, 1183–1199.

Papp, A.C. et al., "Strategies for amplification of trinucleotide repeats: Optimization of fragile X and androgen receptor PCR," *Molecular Diagnosis,* 1996, 1(1), 59–64.

Parsons, R. et al., "Microsatellite instability and mutations of the transforming growth factor β type II receptor gene in colorectal cancer," *Cancer Res,* 1995, 55, 5548–5550.

Potaman, V.N., "Prevention of unexpectedly long PCR products primed at short inverted repeats," *Biotechniques,* 1999, 27, 1110, 1112 and 1114.

Primmer, C.R. et al., "Resolving genetic relationships with microsatellite markers: a parentage testing system for the swallow *Hirundo rustica*," *Mol Ecol.*, 1995, 4, 493–498.

Pyatt, R. et al., "Polymorphic Variation at the BAT–25 and BAT–26 Loci in Individuals of African Origin," *Am J. Pathol.*, 1999; 155(2), 349–353.

Liu, Q. et al., "Subcycling–PCR for multiplex long–distance amplification of regions with high and low GC content: application to the inversion hotspot in the factor VII gene," *Biotechniques,* 1998, 25, 1022–1028.

Rajendrakumar, C.S.V. et al., "DNA helix destabilization by proline and betaine: possible role in the salinity tolerance process," *FEBS Letters,* 1997, 410, 201–205.

Rees, W.A. et al., "Betaine can eliminate the base pair composition dependence of DNA melting," *Biochemistry,* 1993, 32, 137–144.

Rouba, A. et al, "Patterns of allelic loss at the BRCA1 locus in Arabic women with breast cancer," *Int J Mol Med,* 2000, 6(5), 565–9.

Schweitzer, B. et al., "Immunoassays with rolling circle DNA amplification: A versatile platform for ultrasensitive antigen detection," *PNAS,* 2000, 97(18), 10113–10119.

Stewart, I. "Symmetry and chaotic data," *Nature,* 1991, 354, 113.

Tahir, M.A. et al., "DNA typing of samples for polymarker, DQA1, and nine STR loci from a human body exhumed after 27 years," *J Forensic Sci,* 2000, 45(4), 902–7.

Tautz, D., et al., "Cryptic simplicity in DNA is a major source of genetic variation," *Nature,* 1986, 322, 652–656.

Weber, J.L. "Informativeness of human $(dC-dA)_n \cdot (dG-dT)_n$ polymorphisms," *Genomics,* 1990, 7, 524–530.

Weissensteiner, T. et al., "Strategy for controlling preferential amplification and avoiding false negatives in PCR typing," *Biotechniques,* 1996, 21(6), 1100–1108.

Wenz, H. et al., "High–precision genotyping by denaturing capillary electrophoresis," *Genome Res.,* 1998, 8, 69–80.

Zhou et al., "Allelic profiles of mononucleotide repeat microsatellites in control individuals and in colorectal tumors with and without replication errors," *Oncogene,* 1997, 15, 1713–1718.

Ausubel et al., Current Protocols in Molecular Biology, Molecular Cloning, A Laboratory Manual ($3^{rd}$ ed), *John Wiley & Sons,* New York, 1998.

Ausubel et al., Current Protocols In Molecular Biology, *John Wiley & Sons,* 2001.

Kaufman et al.,Eds., Directed Mutagenesis: A Practical Approach, *IRL Press,* 1991.

Kaufman et al., Eds., Handbook of Molecular and Cellular Methods in Biology and Medicine, CRC Press, Boca Raton, 1995.

McPherson, Ed., Directed Mutagenesis: A Practical Approach, *IRL Press,* Oxford, 1991.

Mullis, K.B. et al., Eds. The Polymerase Chain Reaction, Birkhause, Boston, 1994.

Sambrook, J., et al., Eds, Molecular Cloning: A Laboratory Manual ($3^{rd}$Ed), 2001.

* cited by examiner

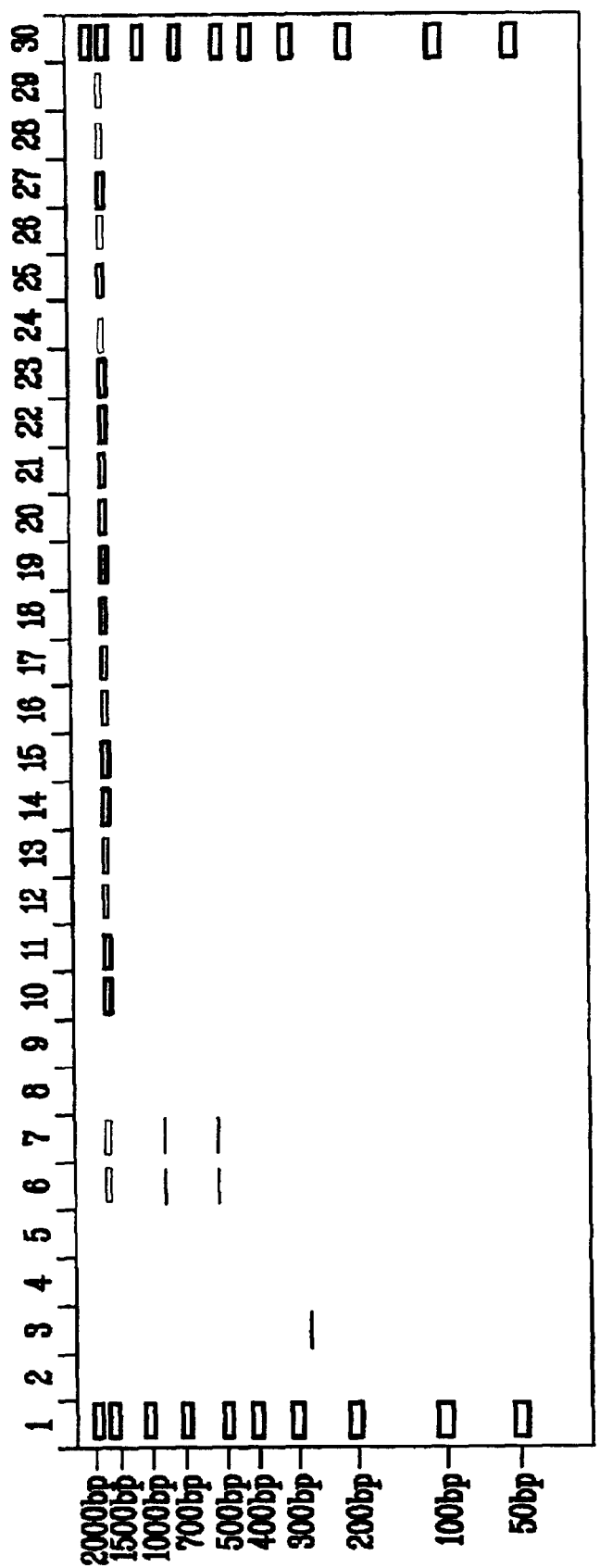

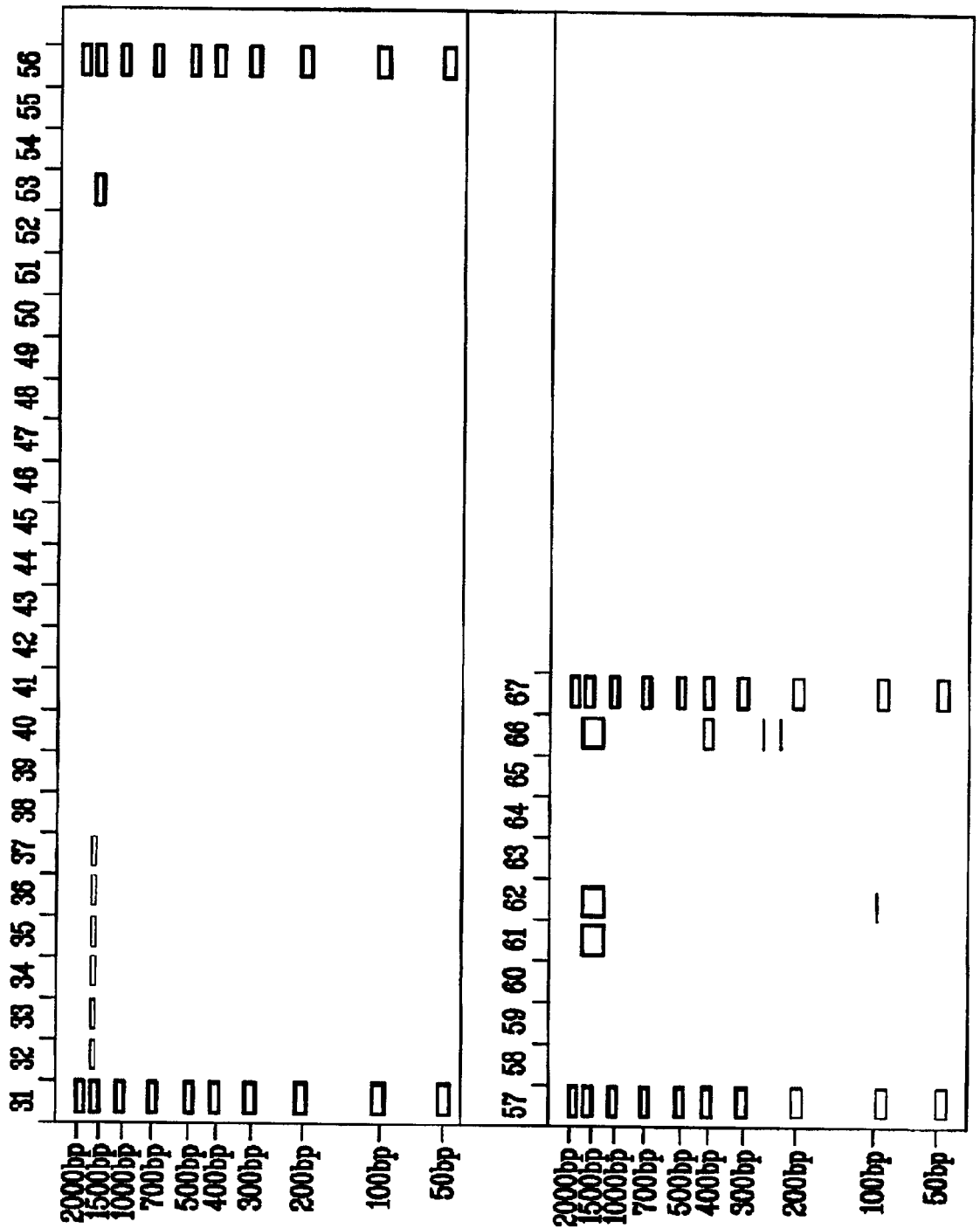

METHOD OF REDUCING NON-SPECIFIC AMPLIFICATION IN PCR

FIELD OF THE INVENTION

The invention is related to reducing non-specific amplification in polymerase chain reactions. Specifically, the invention relates to the use of sorbitol and dimethylsulfoxide (DMSO) in polymerase chain reactions in an amount effective to increase the yield of target molecules.

BACKGROUND OF THE RELATED ART

The polymerase chain reaction (PCR) has greatly advanced the field of molecular biology by allowing the amplification and analysis of specific fragments of DNA. While simple in principle, PCR is prone to several types of artifacts that can frustrate analysis. For example, observed non-specific amplification of fragments may result from one or both of the primers binding to a sequence other than the target sequence, and produce one or more fragments of DNA that are not the desired product.

Non-specific amplification of DNA is often a problem in the amplification of conserved sequences, such as ribosomal DNA. Ribosomal RNA (rRNA) is by far the most abundant species of RNA present in a cell, typically representing 85–90% of the total RNA in a cell. rRNA is encoded by ribosomal DNA (rDNA). Each subunit of rRNA is encoded by a separate rDNA, although multiple rRNA genes exist in most organisms. The mitochondrion of eukaryotes and the chloroplast of plants also contain their own rRNA genes.

Ribosomal RNA has been used in hybridization studies for genetic analysis, evolution studies and taxonomic classification. However, rRNA sequences are at least partially similar in widely different organisms, and nearly all of the rRNA gene sequences from closely related organisms cross-hybridize. In PCR studies, specific amplification of rDNA sequences is difficult due to the relatedness of the sequences. Often, amplification of rDNA in PCR results in non-specific amplification, greatly complicating analysis.

SUMMARY OF THE INVENTION

In accordance with some embodiments of the methods of the invention, methods of reducing non-specific amplification of DNA in a polymerase chain reaction are provided comprising the steps of:
 (a) providing a sample comprising a target DNA sequence of interest;
 (b) contacting said sample with at least one enzyme having nucleic acid polymerase activity; and
 (c) incubating said sample with said enzyme for a time and under conditions sufficient to amplify said target DNA sequence, forming amplified target DNA sequence;
wherein said incubation is performed in the presence of an amount of sorbitol, or sorbitol and DMSO effective to reduce said non-specific amplification relative to the amount of non-specific amplification observed in the absence of sorbitol, or sorbitol and DMSO.

Also provided in some embodiments are methods of amplifying ribosomal DNA in a polymerase chain reaction comprising the steps of:
 (a) providing a sample comprising a ribosomal DNA target sequence of interest; and
 (b) amplifying at least one nucleobase sequence of said ribosomal DNA to form amplified ribosomal DNA in a mixture of total amplified product;
wherein said amplification is performed in the presence of a sufficient amount of sorbitol and DMSO to reduce non-specific amplification relative to the amount of non-specific amplification observed in the absence of said sorbitol and said DMSO.

In some embodiments of the methods of the invention, methods are provided for detecting bacteria in a sample comprising: providing a sample comprising nucleic acid, said nucleic acid comprising at least one ribosomal DNA sequence; and amplifying at least one nucleobase sequence of said nucleic acid, thereby forming an amplified product, wherein said amplification is performed in the presence of an amount of sorbitol effective in reducing non-specific amplification relative to the amount of non-specific amplification observed in the absence of sorbitol. The amplification step may also include an effective amount of DMSO in combination with the sorbitol.

In some embodiments of the methods of the invention, sorbitol may be present in an amount of 0.05 M to 3.0 M. Alternatively, sorbitol may be present in an amount of 0.05 M to 2 M. In other embodiments, sorbitol may be present in an amount of 0.05 to 1 M. In other embodiments, sorbitol is added in an amount of 0.05 M to 0.75 M. In other embodiments, sorbitol may be present in an amount of 0.1 to 0.45 M. In other embodiments, sorbitol may be present in an amount of 0.2 M to 0.4 M. In other embodiments, sorbitol may be present in an amount of 0.25 M to 0.35 M.

In some embodiments of the methods of the invention, DMSO is present in an amount of 0.5% to 8.0%. In other embodiments, DMSO is present in an amount of 1.0% to 6.0%. In other embodiments, DMSO is present in an amount of 2.0% to 5.0%. In other embodiments, DMSO is present in an amount of 3.0% to 4.0%.

In some embodiments of the methods of the invention, DMSO is present in an amount of 1.25% and sorbitol is present in an amount of 0.15 M.

In some embodiments of the methods of the invention, non-specific amplification is reduced to less than 99%, 90%, 80%, 70%, 60%, 50% or 40%, 30%, or more of the amount of non-specific amplification obtained in the absence of sorbitol or sorbitol and DMSO.

In some embodiments of the methods of the invention, the amplified target sequence represents at least 50–70% of said total amplified product. In other embodiments, the amplified target sequence represents at least 70–90% of said total amplified product. In other embodiments, the amplified target sequence represents at least 90% of said total amplified product.

In certain embodiments, the methods of the invention are suitable for reducing non-specific amplification of DNA encoding ribosomal RNA.

The some embodiments of the methods of the invention, amplified products may be subsequently separated using a sieving or non-sieving medium. The nucleic acid sequence of the amplified products may be determined without or without prior separation.

The samples containing ribosomal DNA may be clinical samples such as blood, urine, cerebrospinal fluid, serum, saliva, mucus, skin, gastric secretions and/or stool.

In some embodiments of the methods of the invention, the amplification comprises contacting said nucleobase sequence with an enzyme having a polymerase activity. For example, the enzyme having polymerase activity may be selected from the group consisting of DNA polymerase from *Thermus aquaticus, Thermus thermophilus*, other Thermus species, Bacillus species, Thermococcus species, Thermotoga species, and Pyrococcus species. For example, suitable polymerases include AmpliTaq Gold® DNA polymerase; AmpliTaq® DNA Polymerase; AmpliTaq® DNA Polymerase, Stoffel fragment; rTth DNA Polymerase; rTth DNA Polymerase XL; Bst DNA polymerase large fragment from *Bacillus stearothermophilus*; Vent and Vent Exo- from *Thermococcus litoralis*; Tma from *Thermotoga maritima*; Deep Vent and Deep Vent Exo- and Pfu from Pyrococcus; and mutants, variants and derivatives thereof.

In some embodiments, the invention also provides compositions comprising:
  (a) a nucleic acid sequence comprising a ribosomal DNA;
  (b) at least two primers having a sequence that is complementary to a portion of said nucleic acid sequence adjacent to said ribosomal DNA;
  (c) at least one enzyme having nucleic acid polymerase activity; and
  (d) sorbitol or sorbitol and DMSO.

In other embodiments, the invention provides kits for the amplification of ribosomal DNA comprising, in one or more containers: an agent having polymerase activity, a plurality of deoxynucleotide triphosphates; and sorbitol, and, optionally, DMSO. The polymerase of the kit may be a DNA polymerase from *Thermus aquaticus, Thermus thermophilus*, other Thermus species, Bacillus species, Thermococcus species, Thermotoga species, and Pyrococcus species. For example, suitable polymerases include AmpliTaq Gold® DNA polymerase; AmpliTaq® DNA Polymerase; AmpliTaq® DNA Polymerase, Stoffel fragment; rTth DNA Polymerase; rTth DNA Polymerase XL; Bst DNA polymerase large fragment from *Bacillus stearothermophilus*; Vent and Vent Exo- from *Thermococcus litoralis*; Tma from *Thermotoga maritima*; Deep Vent and Deep Vent Exo- and Pfu from Pyrococcus; and mutants, variants and derivatives thereof.

BRIEF DESCRIPTION OF THE FIGURES

FIG. 4a shows PCR amplifications targeting the 16S rRNA gene in Escherichia coli in the presence of varying amounts of sorbitol, 0.15 M sorbitol and 1.25% DMSO, or no additive, run on an agarose gel. The desired product is at 1500 bp. Lane numbers 1 through 30 are shown.

FIG. 4b shows PCR amplifications targeting the 16S rRNA gene in Escherichia coli in the presence of varying amounts of sorbitol, 0.15 M sorbitol and 1.25% DMSO, or no additive, run on an agarose gel. The desired product is at 1500 bp. Lane numbers 31 through 67 are shown.

DETAILED DESCRIPTION

Figure 1:
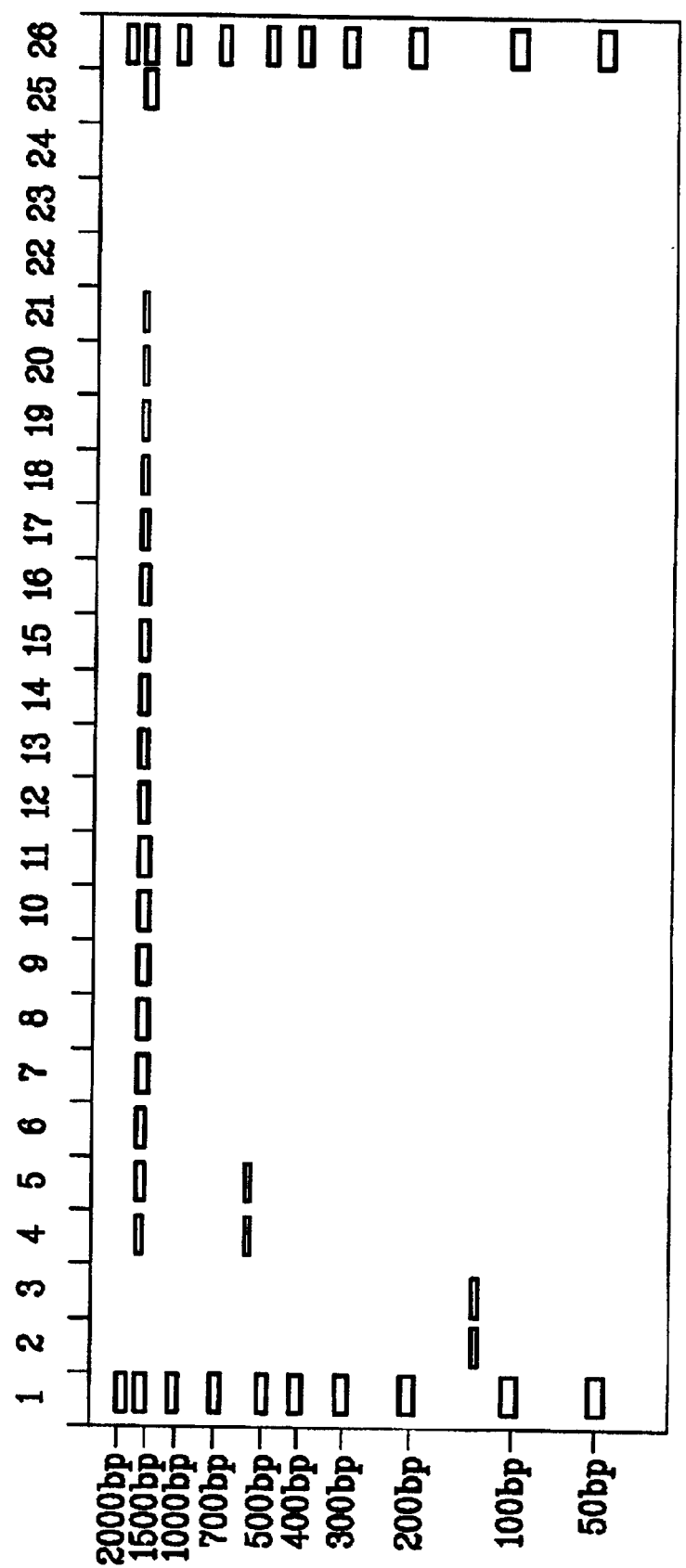
FIG. 1 shows a sorbitol titration in PCR amplifications targeting the 16S rRNA gene in *Escherichia coli* run on an agarose gel. The desired product is at 1500 bp.

The reference works, patents, patent applications, and scientific literature and other printed publications, including accession numbers to GenBank database sequences, that are referred to herein establish the knowledge of those with skill in the art, and are hereby incorporated by reference in their entirety. In the event that a conflict arises between any reference cited herein and the specific teachings of this specification, the specification shall control.

Most of the words used in this specification have the meaning that would be attributed to those words by one skilled in the art. Words specifically defined in the Specification have the meaning provided in the context of the present invention as a whole, and as are typically understood by those skilled in the art. In the event that a conflict arises between an art-understood definition of a word or phrase and a definition of the word or phrase as specifically taught in this specification, the specification shall control. Headings used herein are merely for convenience, and are not to be construed as limiting in any way.

Standard reference works setting forth the general principles of recombinant DNA technology known to those of skill in the art include Ausubel et al., Current Protocols in Molecular Biology, John Wiley & Sons, New York, 1998 Molecular Cloning: A Laboratory Manual (3rd ed.) Sambrook, J. & D. Russell, Eds. Cold Spring Harbor Laboratory Press, Cold Spring Harbor, N.Y. (2001); Kaufman et al., Eds., Handbook of Molecular and Cellular Methods in Biology and Medicine, CRC Press, Boca Raton, 1995; McPherson, Ed., Directed Mutagenesis: A Practical Approach, IRL Press, Oxford, 1991.

As used herein "DMSO" refers to dimethyl sulfoxide.

As used herein "sorbitol" refers to the polyol (polyhydric alcohol) corresponding to glucose, represented by the following structural formula:

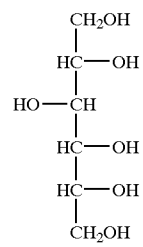

As used herein, the term "isolated nucleic acid molecule" refers to a nucleic acid molecule (DNA or RNA) that has been removed from its native environment.

As used herein, "DNA" refers to deoxyribonucleic acid in its various forms as understood in the art, such as genomic DNA, cDNA, isolated nucleic acid molecules, vector DNA, chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or of chemical precursors or other chemicals when chemically synthesized.

As used herein "rDNA" refers to DNA sequences encoding ribosomal RNA.

As used herein "nucleobase sequence" refers to a sequence of consecutive nucleobases.

As used herein, "non-specific amplification" refers to amplification of a region of DNA that is not the portion of DNA that is the target DNA. As such, non-specific amplification may be amplification of a region of DNA that is unrelated to the target sequence; amplification of a related DNA sequence, but from a different region of DNA than targeted for amplification; or amplification of the target sequence but comprising more or less nucleobases than the intended amplified fragment due to inexact annealing of at least one primer to the target sequence.

As used herein, "anneal" refers to specific interaction between strands of nucleotides wherein the strands bind to one another substantially based on complementarity between the strands as determined by Watson-Crick base pairing. It is not necessary that complementarity be 100% for annealing to occur.

As used herein, "amplifying" refers to enzymatically increasing the amount of a specific nucleotide sequence in a polymerase chain reaction.

As used herein "incubating" refers to a maintaining a state of controlled conditions such as temperature over a period of time.

As used herein "denaturation" refers to the separation of nucleotide strands from an annealed state. Denaturation may be induced by a number of factors including ionic strength of the buffer, temperature, or chemicals that disrupt base pairing interactions.

As used herein, "sufficient amount of time" when referring to time for the amplification of nucleic acid, refers to the time which allows the enzyme used to complete the polymerization of deoxynucleotide triphosphates into the amplifying nucleic acid. The amount of time required varies depending on several factors which are well-known by persons of ordinary skill in the art. General principles of PCR and strategies for amplification may be found in such texts as, for example, Ausubel et al., Current Protocols in Molecular Biology, John Wiley a & Sons, New York, 2001 and The Polymerase Chain Reaction, Mullis, K. B., F. Ferre, and R. A. Gibbs, Eds., Birkhauser, Boston, 1994; and Molecular Cloning: A Laboratory Manual (3rd ed.) Sambrook, J. & D. Russell, Eds. Cold Spring Harbor Laboratory Press, Cold Spring Harbor, N.Y. (2001).

As used herein "conditions sufficient to amplify" refers to reaction conditions for the PCR reactions. The reaction conditions include the chemical components of the reaction, the temperatures used in the reaction cycles, the number of cycles of the reaction, and the time of the stages of the reaction cycles, as is described more fully herein.

Typically, buffered water is used as the milieu for the reaction. The other chemical components of standard PCR reactions include a DNA polymerase, deoxyribonucleoside triphosphates ("dNTPs"), oligonucleotide primers, divalent metal ion, and a DNA sample expected to contain the PCR target.

The solvent used for PCR typically contain a buffering agent such as Tris-HCl and non-buffering salts such as KCl. The buffering agent may be any known buffers in the art, and may be varied to optimize PCR results by routine experimentation. Persons of ordinary skill in the art will readily be able to determine optimal buffering conditions. Some PCR buffers may be optimized depending on the enzyme used. As an example, but not by way of limitation, AmpliTaq Gold® DNA polymerase has an optimum KCl concentration of 50 mM, AmpliTaq® DNA Polymerase, Stoffel fragment has an optimum KCl concentration of 10 mM, and rTth DNA Polymerase and rTth DNA Polymerase XL, have an optimum KCl concentration of 75–100 mM.

Divalent metal ions are often advantageous to allow the polymerase to function efficiently. For example, but not by way of limitation, magnesium ion allows certain DNA polymerases to function effectively. Typically, $MgCl_2$ or $MgSO_4$, is added to reaction buffers to supply the optimum magnesium ion concentration. The magnesium ion concentration required for optimal PCR amplification may depend on the specific set of primers and template used. Thus, the amount of magnesium salt added to achieve optimal amplification is often determined empirically, and is a routine practice in the art. Generally, the concentration of magnesium ion for optimal PCR can vary between 1 and 10 mM. A typical range of magnesium ion concentration in PCR reactions is between 1.0 and 4.0 mM, varying around a midpoint of 2.5 mM.

Deoxynucleotide triphosphates ("dNTPs"), which are the building blocks of the amplifying nucleic acid molecules, are typically supplied in standard PCR reactions at a concentration of 40–200 $\mu$M each of deoxyadenosine triphosphate ("dATP"), deoxyguanosine triphosphate ("dGTP"), deoxycytidine triphosphate ("dCTP") and thymidine triphosphate ("dTTP"). Other dNTPs, such as deoxyuridine triphosphate ("dUTP"), and dNTP analogs, and conjugated dNTPs may also be used, and are encompassed by the term "dNTPs" as used herein. While use of dNTPs at such concentrations are amenable to the methods of the invention, concentrations of dNTPs higher than 200 $\mu$M may be advantageous. Thus, in some embodiments of the methods of the invention, the concentration of dNTPs is generally at least 500 $\mu$M of each dNTP up to 2 mM each. In some further embodiments, concentrations of each dNTP is from 0.5 mM to 1 mM.

The enzyme that polymerizes the nucleotide triphosphates into the amplified fragments of the PCR may be any DNA polymerase, including heat-stable polymerases, known in the art. Polymerases that may be used in the invention include, but are not limited to DNA polymerases from such organisms as *Thermus aquaticus, Thermus thermophilus, Thermococcus litoralis, Bacillus stearothermophilus, Thermotoga maritima* and Pyrococcus ssp. The enzyme may be isolated from the bacteria, produced by recombinant DNA technology or purchased from commercial sources. For example, DNA polymerases are available from Applied Biosystems and include AmpliTaq Gold® DNA polymerase; AmpliTaq® DNA Polymerase; AmpliTaq® DNA Polymerase, Stoffel fragment; rTth DNA Polymerase; and rTth DNA Polymerase XL. Other suitable polymerases include, but are not limited to Tne, Bst DNA polymerase large fragment from *Bacillus stearothermophilus*, Vent and Vent Exo- from *Thermococcus litoralis*, Tma from *Thermotoga maritima*, Deep Vent and Deep Vent Exo- and Pfu from Pyrococcus, and mutants, variants and derivatives of the foregoing.

Oligonucleotide primers are added to the reaction and demarcate the 5' and 3' ends of the amplified fragment. One oligonucleotide primer anneals to the sense (+strand) of the denatured, template DNA, and the other oligonucleotide primer anneals to the antisense (−strand) of the denatured, template DNA. Typically, oligonucleotide primers are 12–25 nucleotides in length, however, they may be shorter or longer depending on the specific template sequence to be amplified, and the length of the primer is not essential to the operation of the invention. Oligonucleotide primers may be designed to anneal to specific portions of DNA that flank a ribosomal RNA gene of interest to specifically amplify the portion of DNA between the primer's complementary sites. Generally, oligonucleotide primers are chemically synthesized. One of ordinary skill in the art may easily design specific primers to amplify a target ribosomal RNA gene of interest. Furthermore, there are many known primer sequences to amplify ribosomal RNA gene regions. Any of these may be used, and are within the scope of the invention.

The oligonucleotide primers may be composed of adenosine, thymidine, guanosine, cytidine, uracil, nucleoside analogs (e.g., locked nucleic acids (LNA), peptide nucleic acid (PNA), phosporamidites) and nucleosides containing or conjugated to chemical moieties such as radionuclides (e.g., $^{32}P$, $^{35}S$), fluorescent molecules, minor groove binders, or any other nucleoside conjugate known in the art.

In some embodiments of the invention, a fluorophore is used to tag at least one primer of the PCR reaction. In some embodiments primers for different target fragments can be tagged with different fluorophores (that produce differently colored products) and may be used in the same multiplex PCR reaction and subsequently analyzed together. Typically, the forward primer is tagged, but the reverse primer may also be tagged. Examples of fluorophores include, but are not limited to, fluorescein (which absorbs maximally at 492 nm and emits maximally at 520 nm); TAMRA, N,N,N',N'-tetramethyl-6-carboxyrhodamine (which absorbs maximally at 555 nm and emits maximally at 580 nm); FAM, 5-carboxyfluorescein (which absorbs maximally at 495 nm and emits maximally at 525 nm); JOE, 2',7'-dimethoxy-4', 5'-dichloro-6-carboxyfluorescein (which absorbs maximally at 525 nm and emits maximally at 555 nm), ROX, 6-carboxy-X-rhodamine (which absorbs maximally at 585 nm and emits maximally at 605 nm); CY3 (which absorbs maximally at 552 nm and emits maximally at 570 nm), CY5 (which absorbs maximally at 643 nm and emits maximally at 667 nm); TET, tetrachloro-fluorescein (which absorbs maximally at 521 nm and emits maximally at 536 nm); and HEX, hexachloro-fluorescein (which absorbs maximally at 535 nm and emits maximally at 556 nm).

Other known components of PCR reactions may be used within the scope of the invention. Such components include, but are not limited to, detergents (e.g., Triton X-100, Nonidet P-40 (NP-40), Tween-20) and agents that disrupt mismatching of nucleotide pairs, such as dimethylsulfoxide (DMSO), and tetramethylammonium chloride (TMAC).

The PCR reactions may also be performed in the presence of other reagents to optimize amplification. For example, but not by way of limitation, uracil N-glycosylase (UNG), such as included in the GeneAmp® PCR Carry-over Prevention Kit may be used. UNG may be included in the PCR reaction as an initial step to ensure that PCR products cannot be reamplified in subsequent PCR amplifications. The principle is based on an enzymatic reaction analogous to the restriction-modification and excision-repair systems of cells. PCR products from previous PCR amplifications in which dUTP has been incorporated are degraded. Native nucleic acid templates are unaffected. The method involves substituting dUTP for dTTP in the PCR mixture, and pretreating all subsequent PCR mixtures with the uracil N-glycosylase enzyme prior to PCR amplification. Uracil is excised from initial products using UNG and are eliminated by degrading the resulting abasic polynucleotide with heat.

PCR reaction time, temperatures and cycle numbers may be varied to optimize a particular reaction as a matter of routine experimentation. Those of ordinary skill in the art will recognize the following as guidance in determining the various parameters for PCR reactions, and also will recognize that variation of one or more conditions is within the scope of the invention.

PCR reaction temperature and time is determined in three stages: denaturation, annealing and extension. One round of denaturation, annealing and extension is referred to as a "cycle." Denaturation is generally conducted at a temperature that permits the strands of DNA to separate, yet not destroy the activity of the polymerase. Generally, thermostable polymerases are used. However, heat-labile polymerases may be used if they are replenished after the denaturation step of the PCR. Thermostable polymerases can withstand high temperatures and maintain some level of activity. Typically, denaturation is conducted above 90° C. and below 100° C. In some embodiments, denaturation is conducted at a temperature of 94–95° C. Denaturation of DNA is generally conducted for at least 1 to 30 seconds. In some embodiments, denaturation is conducted for 1 to 15 seconds. In other embodiments, denaturation is conducted for up to 1 minute or more. In addition to the denaturation of DNA, for some polymerases, such as AmpliTaq Gold®, incubation at the denaturation temperature also serves to activate the enzyme. Therefore, it may be advantageous to allow the first step of PCR (denaturation) to be longer than subsequent denaturation steps when these enzymes are used.

During the annealing phase, oligonucleotide primers anneal to the target DNA in their regions of complementarity and are substantially extended by the DNA polymerase once the latter has bound to the primer-template duplex.

In a conventional PCR, the annealing temperature typically is at or below the melting point ($T_m$) of the least stable primer-template duplex, where $T_m$ can be estimated by any of several theoretical methods well known to practitioners of the art. For example, the $T_m$ may be determined by the formula:

$$T_m = (4° \text{ C.} \times \text{number of } G \text{ and } C \text{ bases}) + (2° \text{ C.} \times \text{number of } A \text{ and } T \text{ bases})$$

Typically, in standard PCRs, the annealing temperature is 5° C. to 10° C. below the estimated $T_m$ of the least stable primer-template duplex. The annealing time is between about 30 seconds and 2 minutes. However, in certain embodiments of the methods of the invention, the high concentration of sorbitol increases reagent viscosity and appears to slow certain steps of the reaction (e.g., primer annealing and polymerase binding to the primer-template duplex). Thus, in certain embodiments of the methods of the invention, the annealing step is performed for a longer period of time than would be used in standard PCR protocols, typically for at least 3 minutes and as long as 5 to 6 minutes. In some embodiments the annealing time may be increased to 10 minutes.

Sorbitol not only increases reaction viscosity, but also is a mild DNA denaturant. Thus, in certain embodiments of the methods of the invention, it is may be advantageous to use a lower temperature for annealing primers to the template than would be used by one of ordinary skill in the art for standard PCR reactions. In general, temperatures lower than 10° C. below the $T_m$ (estimated in the absence of additive) may be employed in certain embodiments of the invention. In other embodiments, temperatures of 20° C. below the $T_m$ (estimated in the absence of additive) may be employed.

The annealing phase typically is followed by an extension phase. "Extension" is conducted for a sufficient amount of time to allow the enzyme to complete primer extension into the appropriately sized fragments. As discussed above, the addition of a high concentration of sorbitol increases the viscosity of the reaction, making unconventionally long extension times advantageous in certain embodiments of the methods of the invention; i.e., the use of extension times that are longer compared to extension times one of ordinary skill in the art would calculate for standard PCR reactions.

Furthermore, as noted above for the annealing phase, sorbitol is a mild denaturant. Thus, in some embodiments of the methods of the invention, it may be advantageous to also use a lower temperature for extension than would be used by one of ordinary skill in the art for standard PCR reactions. Thus, for some embodiments, temperatures for extension are below the temperature reported for optimal activity of the polymerases used.

The number of cycles of PCR (denaturation, annealing and extension) used will determine the desired amount of amplification. PCR is an exponential amplification of DNA molecules. Thus, theoretically, after each cycle of PCR, there are twice the number of fragments that were present in the prior cycle. Typically, 20–30 cycles of PCR are performed. More typically, 25–30 cycles are performed, although cycle number is not particularly limited.

For some embodiments, it is advantageous to incubate the reactions at a certain temperature following the last phase of the last cycle of PCR. In some embodiments, a prolonged extension phase is selected. In other embodiments, an incubation at a low temperature (e.g., 4° C.) is selected.

In some embodiments of the present invention, PCR is performed in the presence of sorbitol alone, or sorbitol and a denaturant, such as DMSO to increase the yield of specifically amplified target DNA sequences, such as ribosomal DNA sequences. While not wishing to be bound to any particular theory of operation, it is believed that sorbitol increases specific product yield and assay sensitivity when amplifying DNA, and that the addition of DMSO further improves specific product yield.

In some embodiments of the methods of the invention, stereoisomers of polyols having the formula $C_nO_nH_n+2$, where $2<n<7$, can be used in an amount of 0.05M to 3 M, 0.05 M to 2M, 0.05 to 1 M, 0.05 to 0.75 M, or 0.05 M to 0.45 M. In some embodiments of the methods of the invention, the polyol is sorbitol. In some embodiments of the methods of the invention, sorbitol is added in an amount of effective to reduce non-specific amplification relative to the amount of non-specific amplification observed in the absence of sorbitol. Typically, sorbitol is added in an amount of 0.05 M to 3 M. In some embodiments, sorbitol is added in an amount of 0.05 M to 2 M. In other embodiments, sorbitol is added in an amount of 0.05 M to 1 M. In other embodiments, sorbitol is added in an amount of 0.05 M to 0.75 M. In other embodiments, sorbitol is added in an amount of 0.05 M to 0.45 M. In other embodiments of the methods of the invention, sorbitol is added in an amount of 0.05 M to 0.40 M. In other embodiments of the methods of the invention, sorbitol is added in an amount of 0.15M to 0.35 M. In other embodiments of the methods of the invention, sorbitol is added in an amount of 0.2 M to 0.3 M.

The addition of a denaturant to PCRs may also increase specific target yield. Denaturants suitable for use in the methods of the invention include, but are not limited to DMSO, 2-pyrrolidinine, and 1-methyl-2-pyrrolidinone. Other denaturants can be found in, for example, the Sigma Catalog (2000–2001) Sigma-Aldrich Fine Chemicals, P.O. Box 14508, St. Louis, Mo. 63178. Denaturants may be added in an amount of 0.75% to 7.0% (vol/vol), 1.0% to 6% (vol/vol), 1.5% to 5.0% (vol/vol), or 2.0% to 4.0% (vol/vol). In some embodiments of the methods of the invention, typically, DMSO is in an amount of 0.75% to 7.0% (vol/vol). In some embodiments of the methods of the invention, DMSO is added in an amount of 1.0% to 6.0% (vol/vol). In other embodiments of the methods of the invention, DMSO is added in an amount of 1.5% to 5.0% (vol/vol). In other embodiments of the methods of the invention, DMSO is added in an amount of 2.0% to 4.0% (vol/vol).

The polyol and denaturant, such as sorbitol and DMSO, may be added in combination over the ranges provided above for each, in any combination. In certain embodiments of the methods of the invention, for example, sorbitol is added in an amount of 0.05 M to 3 M sorbitol in combination with 0.75% to 7% (vol/vol) DMSO. In other embodiments of the methods of the invention, sorbitol is added in an amount of 0.1 M to 2M and DMSO is added in an amount of 1% to 6% (vol/vol). In other embodiments of the methods of the invention, sorbitol is added in an amount of 0.15 M to 1 M with DMSO in an amount of 1.25% to 5% (vol/vol). In other embodiments of the methods of the invention, sorbitol is added in an amount of 0.2 M to 0.75 with DMSO in an amount of 1.5% to 3% (vol/vol). In some embodiments of the invention shown in the Examples, sorbitol is added in an amount of 0.15 M and DMSO is added in an amount of 1.25% (vol/vol).

When performing PCR using sorbitol at the higher concentrations (above 1 M), it may be advantageous to increase the annealing time and/or decrease the annealing temperature to optimize the PCR reaction and product yield. One of ordinary skill in the art should be able to readily optimize reaction conditions for time and temperature of annealing to complement the amount of sorbitol and/or DMSO added. In general, the temperature of annealing should not have to be less than 20° C. below the $T_m$ (estimated in the absence of additive). Further, in general, the annealing time should not have to be more than 10 minutes (estimated in the absence of additive).

In some embodiments, sorbitol and DMSO may be added to PCRs to amplify rDNA from a wide variety of organisms, particularly bacteria. Bacterial rDNA is unique to each species. Therefore, the methods of the invention also encompass amplification of rDNA coupled with sequencing of the amplified product. The sequence obtained in this manner may be compared to the sequences known for bacterial rDNA to precisely identify a bacterial species present in a sample.

In one embodiment of the methods of the invention, a sample containing genomic DNA is added to a master PCR mix comprising buffered water, $Mg^{2+}$, polymerase, dNTPs, rDNA forward and reverse primers, and sorbitol, or sorbitol and DMSO, and an amplification is performed. The amplified product is added to a sequencing reaction, such as, for example, a single step sequencing mix (available through Applied Biosystems), and the sequence is compared to a 16s rDNA library (such as the proprietary MicroSeq™ 16S rDNA sequence library of Applied Biosystems).

In some embodiments, the PCR product is separated using a non-sieving medium prior to sequencing. In other embodiments, the PCR product is separated in a sieving medium prior to sequencing.

Reduction of non-specific amplification may be determined by any means known in the art. As a non-limiting example, observance of an increased amount of correctly sized product on a gel may be visualized and quantified by measuring intensity. Further, other non-specific products visualized as bands on a gel with a non-predicted size may be reduced in intensity, or eliminated. That is, in the absence of sorbitol or sorbitol and DMSO in the PCR reactions, a non-specific amplified product may appear as an intense band on an agarose gel and running as an incorrectly sized fragment. Whereas the specific amplified product may appear as a correctly sized fragment, but appear less intense relative to other products. When sorbitol or sorbitol and DMSO are added to the PCR reactions, the incorrectly sized (non-specific) amplification product will appear less intense (or be absent), while the correctly sized, specific product will appear more intense relative to any non-specifically amplified products.

The invention will be further described using the following actual examples, which are merely illustrative of some embodiments of the invention. The examples should not be construed in any way to limit the scope of the invention, which is defined by the appended claims.

EXAMPLES

Example 1

A titration for suitable amounts of sorbitol to reduce non-specific amplification of 16S ribosomal DNA was performed for the *Escherichia coli* 16S rRNA gene. 50 pg of *E. coli* DNA was subjected to PCR using the amplification step of the MicroSeq™ 16S rRNA Gene Kit in which PCR reactions are set up as follows: (a) negative controls, 50 µl PCR Master Mix, 50 µl sterile deionized water; (b) positive controls, 50 µl PCR Master Mix, 50 µl positive control DNA; (c) samples, 50 µl PCR Master Mix, 50 µl of 50 ng diluted *E. coli* DNA. Furthermore, each reaction contained AmpErase® Uracil N-glycosylase (UNG). Typically, UNG may be added in an amount of 0.5 to 2 units/reaction. The initial amplifications were performed as follows: 50° C. for 10 minutes, 95° C. for 10 minutes, followed by 35 cycles of 95° C. for 30 seconds, 60° C. for 30 seconds and 72° C. for 45 seconds; followed by a final extension step at 72° C. for 10 minutes, and thereafter, the reactions were immediately analyzed or maintained at −20° C. The PCR Master Mix contained DNA Polymerase, dNTPs, and optimized buffer components.

Upon completion of the PCRs, 5 µl of each reaction was run on a 2% NuSieve, 0.5% SeaKem agarose gel with ethidium bromide in the gel and running buffer (0.5 µg/ml) and visualized by ultraviolet light.

With reference to FIG. 1, the reactions contained no sorbitol (lanes 2 and 3); 0.05 M sorbitol (lanes 4 and 5); 0.10 M sorbitol (lanes 6 and 7); 0.15 M sorbitol (lanes 8 and 9); 0.20 M sorbitol (lanes 10 and 11); 0.25 M sorbitol (lanes 12 and 13); 0.30 M sorbitol (lanes 14 and 15); 0.35 M sorbitol (lanes 16 and 17); 0.40 M sorbitol (lanes 18 and 19); 0.45 M sorbitol (lanes 20 and 21); no template DNA added (lanes 22, 23 and 24); 50 ng *E. coli* DNA template (lane 25); and 10 ng/band/µL of 50–2,000 bp ladder (lanes 1 and 26). The results are shown in FIG. 1. Notably sorbitol at a concentration of 0.15 M (lanes 8 and 9) showed substantial increase in specific target DNA (about 1500 bp) while also showing an absence of the non-specific band at about 140 bp.

Example 2

A titration for suitable amounts of DMSO to reduce non-specific amplification of 16S ribosomal DNA was performed for the *Escherichia coli* 16S rRNA gene. 50 pg of *E. coli* DNA was subjected to PCR using the amplification step of the MicroSeq™ 16S rRNA Gene Kit in which PCR reactions were set up as follows: (a) negative controls, 50 µl PCR Master Mix, 50 µl sterile deionized water; (b) positive controls, 50 µl PCR Master Mix, 50 µl positive control DNA; (c) samples, 50 µl PCR Master Mix, 50 µl of 50 ng diluted *E. coli* DNA. Furthermore, each reaction contained AmpErase® Uracil N-glycosylase (UNG). Typically, UNG may be added in an amount of 0.5 to 2 units/reaction. The initial amplifications were performed as follows: 50° C. for 10 minutes, 95° C. for 10 minutes, followed by 35 cycles of 95° C. for 30 seconds, 60° C. for 30 seconds and 72° C. for 45 seconds; followed by a final extension step at 72° C. for 10 minutes, and thereafter the reactions were either analyzed immediately, or maintained at −20° C. The PCR Master Mix contained DNA Polymerase, dNTPs, and optimized buffer components.

Upon completion of the PCRs, 5 µl of each reaction was run on a 2% NuSieve, 0.5% SeaKem agarose gel with ethidium bromide in the gel and running buffer (0.5 µg/ml) and visualized by ultraviolet light.

Figure 2:
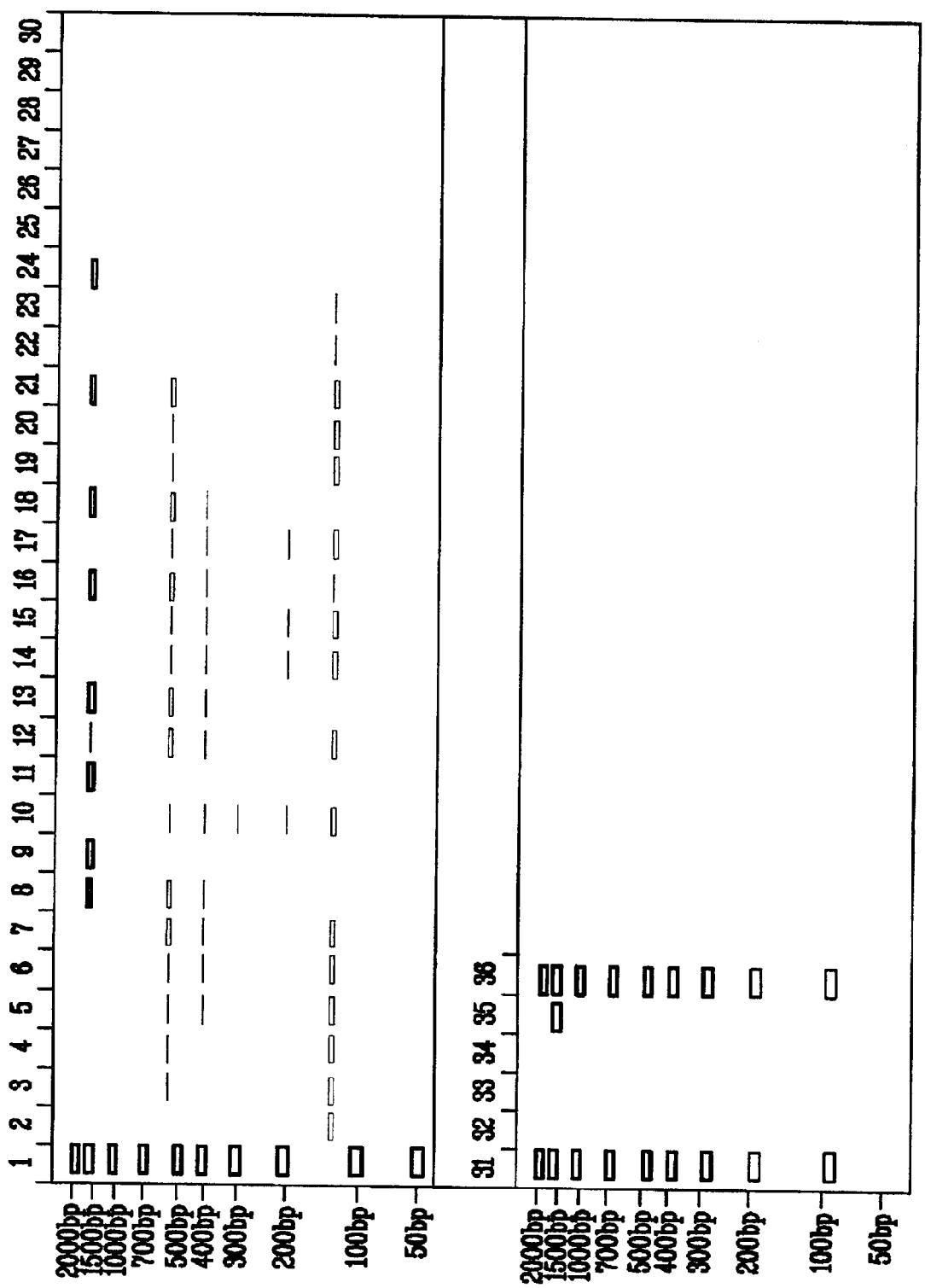
FIG. 2 shows a DMSO titration in PCR amplifications targeting the 16S rRNA gene in *Escherichia coli* run on an agarose gel. The desired product is at 1500 bp.

With reference to FIG. 2, the reactions contained either no DMSO (lane 2); 0.25% DMSO (lanes 3 and 4); 0.50% DMSO (lanes 5 and 6); 0.75% DMSO (lanes 7 and 8); 1.00% DMSO (lanes 9 and 10); 1.50% DMSO (lanes 11 and 12); 2.00% DMSO (lanes 13 and 14); 3.00% DMSO (lanes 15 and 16); 4.00% DMSO (lanes 17 and 18); 5.00% DMSO (lanes 19 and 20); 6.00% DMSO (lanes 21 and 22); 7.00% DMSO (lanes 23 and 24); 8.00% DMSO (lanes 25 and 26); 9.00% DMSO (lanes 27 and 28); 10.00% DMSO (lanes 29 and 30); no template DNA added (lanes 32, 33 and 34); 50 ng *E. coli* DNA template (lane 35); and 10 ng/band/µL of 50–2,000 bp ladder (lanes 1, 31 and 36). The results are shown in FIG. 2. Notably DMSO at a concentration of 1.00% and 1.5% (lanes 9 and 11) showed substantial increase in specific target DNA (about 1500 bp) while also showing an absence of the non-specific band at about 140 bp and other bands.

Example 3

The effect of adding sorbitol and DMSO to reduce non-specific amplification of 16S ribosomal DNA was performed for the *Escherichia coli* 16S rRNA gene. 5, 50, or 500 pg of *E. coli* DNA was subjected to PCR using the amplification step of the MicroSeq™ 16S rRNA Gene Kit in the presence of 0.15M sorbitol, or 0.15 M sorbitol+1.25% (vol/vol) DMSO. The PCR reactions were set up as follows: (a) negative controls, 50 µl PCR Master Mix, 50 µl sterile deionized water; (b) positive controls, 50 µl PCR Master Mix, 50 µl positive control DNA; (c) samples, 50 µl PCR Master Mix, 50 µl of 50 ng diluted *E. coli* DNA. Furthermore, each reaction contained AmpErase® Uracil N-glycosylase (UNG). Typically, UNG may be added in an amount of 0.5 to 2 units/reaction. The initial amplifications were performed as follows: 50° C. for 10 minutes, 95° C. for 10 minutes, followed by 30 cycles of 95° C. for 30 seconds, 60° C. for 30 seconds and 72° C. for 45 seconds; followed by a final extension step at 72° C. for 10 minutes, and thereafter the reactions were either analyzed immediately, or maintained at −20° C. The PCR Master Mix contained DNA Polymerase, dNTPs, and optimized buffer components.

Upon completion of the PCRs, 5 µl of each reaction was run on a standard agarose gel (1% agarose in TBE buffer (Tris-HCl, Boric acid, EDTA), staining with ethidium bromide, and visualized by ultraviolet light.

Figure 3:
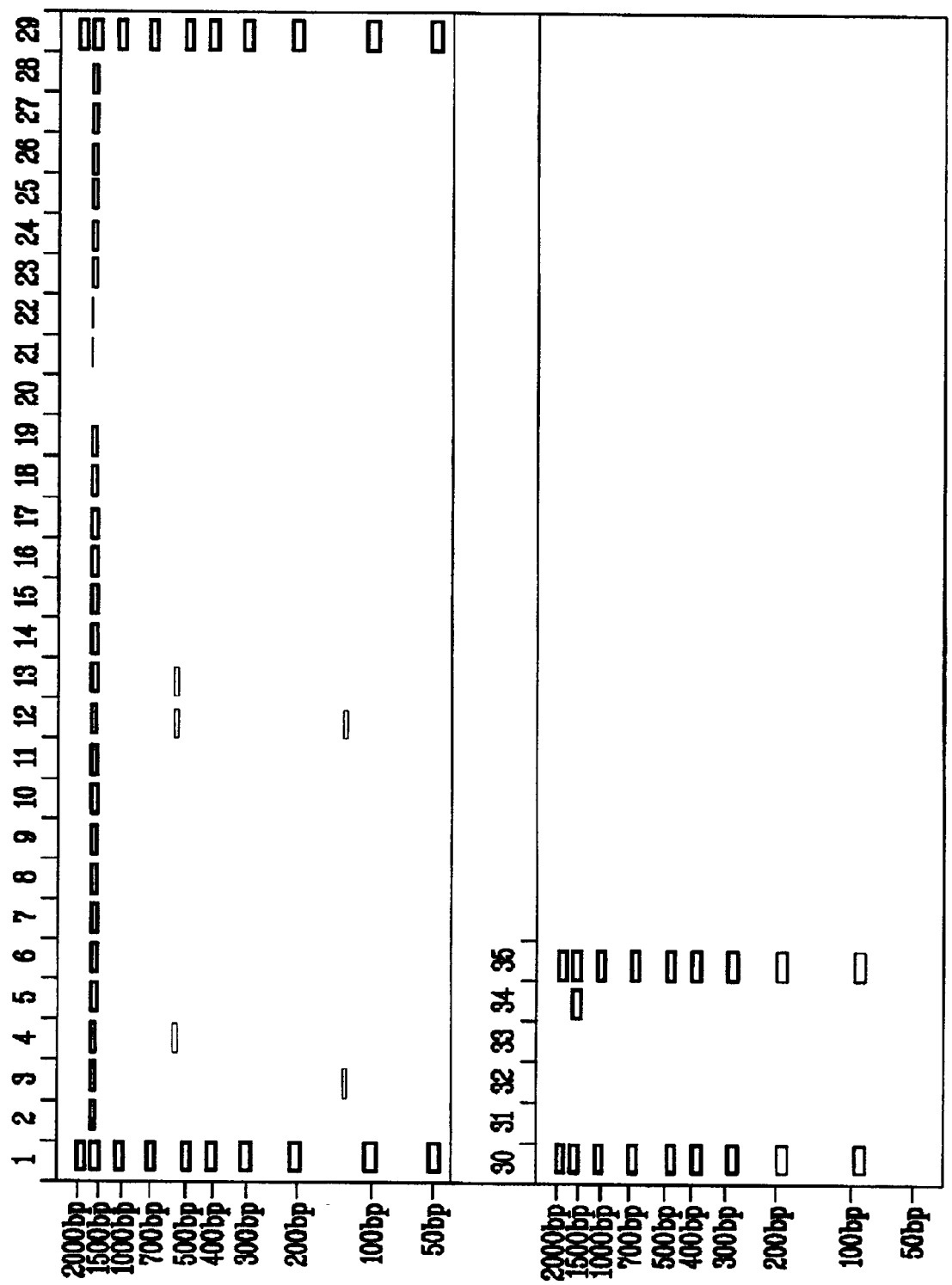
FIG. 3 shows PCR amplifications targeting the 16S rRNA gene in *Escherichia coli* in the presence of a combination of sorbitol (0.15M) and DMSO (1.25%) run on an agarose gel. The desired product is at 1500 bp.

With reference to FIG. 3, the reactions contained: 500 pg DNA template and no DMSO or sorbitol (lanes 2, 3 and 4); 500 pg DNA template and 0.15 M sorbitol only (lanes 5, 6 and 7); 500 pg DNA template and 0.15 M sorbitol and 1.25% DMSO (lanes 8, 9, and 10); 50 pg DNA template and no DMSO or sorbitol (lanes 11, 12 and 13); 50 pg DNA template and 0.15 M sorbitol only (lanes 14, 15 and 16); 50 pg DNA template and 0.15 M sorbitol and 1.25% DMSO (lanes 17, 18, and 19); 5 pg DNA template and no DMSO or sorbitol (lanes 20, 21 and 22); 5 pg DNA template and 0.15 M sorbitol only (lanes 23, 24 and 25); 5 pg DNA template and 0.15 M sorbitol and 1.25% DMSO (lanes 26, 27, and 28); no template DNA added (lanes 31, 32 and 33); 50 ng *E.* coli DNA template (lane 34); and 10 ng/band/µL of 50–2,000 bp ladder (lanes 1, 29, 30, and 35). The results are shown in FIG. 3. Notably, an increase in sensitivity is seen in this experiment as specific amplification product from 5 pg of positive control DNA template is detected with the addition of sorbitol or sorbitol and DMSO (lanes 23 through 28).

Example 4

The effect of adding varying amounts of sorbitol or sorbitol and DMSO to reduce non-specific amplification of 16S ribosomal DNA was performed for the *Escherichia coli* 16S rRNA gene. 5 pg, 50 pg, or 66 fg of *E. coli* DNA was subjected to PCR using the amplification step of the MicroSeq™ 16S rRNA Gene Kit in the presence of 0.05 M, 0.15 M, 0.25 M, 0.35 M, 0.45 M, 0.55 M, 0.65 M, 0.75 M, 1.0 M, or 2.0 M sorbitol; 0.15M sorbitol and 1.25% DMSO (vol/vol); or no additive. The PCR reactions were set up as follows: (a) negative controls, 50 µl PCR Master Mix, 50 µl sterile deionized water; (b) positive controls, 50 µl PCR Master Mix, 50 µl positive control DNA; (c) samples, 50 µl PCR Master Mix, 50 µl of 50 ng diluted *E. coli* DNA. Furthermore, each reaction contained AmpErase® Uracil N-glycosylase (UNG). Typically, UNG may be added in an amount of 0.5 to 2 units/reaction. The initial amplifications were performed as follows: 50° C. for 10 minutes, 95° C. for 10 minutes, followed by 30 cycles of 95° C. for 30 seconds, 50° C. (or 56° C.) for 2 minutes and 72° C. for 3 minutes; followed by a final extension at 72° C. for 10 minutes, and thereafter the reactions were either analyzed immediately, or maintained at −20° C. The PCR Master Mix contained DNA Polymerase, dNTPs, and optimized buffer components.

The reactions were set up according to Table 1 and loaded as shown in FIGS. 4a and 4b. In this experiment, compared to FIG. 1 performed with standard thermocycling conditions, the effective upper limit in the concentration range of sorbitol was increased from about 0.45 M to 0.75 M with an annealing temperature of 56° C. Product yield is consistently lower using an annealing temperature of 50° C., and the effective upper limit in the sorbitol concentration range is increased to 0.65 M.

TABLE 1

PCR reactions

| Lane No. | Annealing Temperature | Reaction components |
|---|---|---|
| 1 | | 10 ng/band/µL of 50–2,000 bp ladder |
| 2 | 56° C. | no additive |
| 3 | 56° C. | no additive |
| 4 | 50° C. | no additive |
| 5 | 50° C. | no additive |
| 6 | 56° C. | 0.05 M sorbitol |
| 7 | 56° C. | 0.05 M sorbitol |
| 8 | 50° C. | 0.05 M sorbitol |
| 9 | 50° C. | 0.05 M sorbitol |
| 10 | 56° C. | 0.15 M sorbitol |
| 11 | 56° C. | 0.15 M sorbitol |
| 12 | 50° C. | 0.15 M sorbitol |
| 13 | 50° C. | 0.15 M sorbitol |
| 14 | 56° C. | 0.25 M sorbitol |
| 15 | 56° C. | 0.25 M sorbitol |
| 16 | 50° C. | 0.25 M sorbitol |
| 17 | 50° C. | 0.25 M sorbitol |
| 18 | 56° C. | 0.35 M sorbitol |
| 19 | 56° C. | 0.35 M sorbitol |
| 20 | 50° C. | 0.35 M sorbitol |
| 21 | 50° C. | 0.35 M sorbitol |

TABLE 1-continued

PCR reactions

| Lane No. | Annealing Temperature | Reaction components |
|---|---|---|
| 22 | 56° C. | 0.45 M sorbitol |
| 23 | 56° C. | 0.45 M sorbitol |
| 24 | 50° C. | 0.45 M sorbitol |
| 25 | 50° C. | 0.45 M sorbitol |
| 26 | 56° C. | 0.55 M sorbitol |
| 27 | 56° C. | 0.55 M sorbitol |
| 28 | 50° C. | 0.55 M sorbitol |
| 29 | 50° C. | 0.55 M sorbitol |
| 30 | | 10 ng/band/µL of 50–2,000 bp ladder |
| 31 | | 10 ng/band/µL of 50–2,000 bp ladder |
| 32 | 56° C. | 0.65 M sorbitol |
| 33 | 56° C. | 0.65 M sorbitol |
| 34 | 50° C. | 0.65 M sorbitol |
| 35 | 50° C. | 0.65 M sorbitol |
| 36 | 56° C. | 0.75 M sorbitol |
| 37 | 56° C. | 0.75 M sorbitol |
| 38 | 50° C. | 0.75 M sorbitol |
| 39 | 50° C. | 0.75 M sorbitol |
| 40 | 56° C. | 1.0 M sorbitol |
| 41 | 56° C. | 1.0 M sorbitol |
| 42 | 50° C. | 1.0 M sorbitol |
| 43 | 50° C. | 1.0 M sorbitol |
| 44 | 56° C. | 2.0 M sorbitol |
| 45 | 56° C. | 2.0 M sorbitol |
| 46 | 50° C. | 2.0 M sorbitol |
| 47 | 50° C. | 2.0 M sorbitol |
| 48 | 56° C. | 0.15 M sorbitol, 66 fg positive control DNA template |
| 49 | 56° C. | 0.15 M sorbitol, 66 fg positive control DNA template |
| 50 | 50° C. | 0.15 M sorbitol, 66 fg positive control DNA template |
| 51 | 50° C. | 0.15 M sorbitol, 66 fg positive control DNA template |
| 52 | 56° C. | 0.15 M sorbitol + 1.25% DMSO, 66 fg positive control DNA template |
| 53 | 56° C. | 0.15 M sorbitol + 1.25% DMSO, 5 pg positive control DNA template |
| 54 | 50° C. | 0.15 M sorbitol + 1.25% DMSO, 66 fg positive control DNA template |
| 55 | 50° C. | 0.15 M sorbitol + 1.25% DMSO, 66 fg positive control DNA template |
| 56 | | 10 ng/band/µL of 50–2,000 bp ladder |
| 57 | | 10 ng/band/µL of 50–2,000 bp ladder |
| 58 | 56° C. | negative control: no DNA template, 0.15 M sorbitol |
| 59 | 56° C. | negative control: no DNA template, 0.15 M sorbitol |
| 60 | 56° C. | negative control: no DNA template, 0.15 M sorbitol |
| 61 | 56° C. | positive control: 50 ng *E. coli* DNA template; 0.15 M sorbitol |
| 62 | 56° C. | positive control: 50 ng *E. coli* DNA template |
| 63 | 50° C. | negative control: no DNA template, 0.15 M sorbitol |
| 64 | 50° C. | negative control: no DNA template, 0.15 M sorbitol |
| 65 | 50° C. | negative control: no DNA template, 0.15 M sorbitol |
| 66 | 50° C. | positive control: 50 ng *E. coli* DNA template |
| 67 | | 10 ng/band/µL of 50–2,000 bp ladder |

What is claimed is:

1. A method for reducing non-specific amplification of DNA in a polymerase chain reaction comprising the steps of:
    (a) providing a sample comprising a target DNA sequence of interest;
    (b) contacting said sample with at least one enzyme having nucleic acid polymerase activity; and
    (c) incubating said sample with said enzyme for a time and under conditions sufficient to amplify said target DNA sequence, forming amplified target DNA sequence;
wherein said incubation is performed in the presence of an amount of sorbitol and an amount of DMSO effective to reduce said non-specific amplification relative to the amount of non-specific amplification observed in the absence of sorbitol and DMSO, wherein said non-specific amplification is amplification of a region of DNA that is unrelated to said target sequence, amplification of a related but different DNA sequence than the target DNA sequence, or amplification of the target sequence with inexact annealing of at least one primer to said target DNA sequence.

2. The method of claim 1 wherein the sorbitol is present in an amount of 0.05 M to 3 M.

3. The method of claim 1 wherein the sorbitol is present in an amount of 0.1 M to 2 M.

4. The method of claim 1 wherein the sorbitol is present in an amount of 0.2 M to 1 M.

5. The method of claim 1 wherein the sorbitol is present in an amount of 0.25 M to 0.5 M.

6. The method of claim 1 wherein said DMSO is present in an amount of 0.5% to 8.0%.

7. The method of claim 1 wherein said DMSO is present in an amount 1.0% to 6.0%.

8. The method of claim 1 wherein said DMSO is present in an amount of 2.0% to 5.0%.

9. The method of claim 1 wherein said DMSO is present in an amount of 3.0% to 4.0%.

10. The method of claim 1 wherein said DMSO is present in an amount of 1.25% and said sorbitol is present in an amount of 0.15 M.

11. The method of claim 1 wherein said non-specific amplification is reduced to less than 99% or more of the amount of non-specific amplification obtained in the absence of said sorbitol and DMSO.

12. The method of claim 1 wherein said non-specific amplification is reduced to less than 90% of the amount of non-specific amplification obtained in the absence of said sorbitol and DMSO.

13. The method of claim 1 wherein said non-specific amplification is reduced to less than 80% of the amount of non-specific amplification obtained in the absence of said sorbitol and DSMO.

14. The method of claim 1 wherein said non-specific amplification is reduced to less than 70% of the amount of non-specific amplification obtained in the absence of said sorbitol and DMSO.

15. The method of claim 1 wherein said non-specific amplification is reduced to less than 60% of the amount of non-specific amplification obtained in the absence of said sorbitol and DMSO.

16. The method of claim 1 wherein said non-specific amplification is reduced to less than 50% of the amount of non-specific amplification obtained in the absence of said sorbitol and DMSO.

17. The method of claim 1 wherein said non-specific amplification is reduced to less than 40% of the amount of non-specific amplification obtained in the absence of said sorbitol and DMSO.

18. The method of claim 1 wherein said non-specific amplification is reduced to less than 30% of the amount of non-specific amplification obtained in the absence of said sorbitol and DMSO.

19. The method of claim 1 wherein said amplified target sequence represents at least 50–70% of said total amplified product.

20. The method of claim 1 wherein said amplified target sequence represents at least 70–90% of said total amplified product.

21. The method of claim 1 wherein said amplified target sequence represents at least 90% of said total amplified product.

22. The method of claim 1 wherein said DNA encodes ribosomal RNA.

23. The method of claim 1 wherein said DNA encodes ribosomal RNA.

24. The method of claim 1 wherein said amplification comprises contacting said nucleobase sequence with an enzyme having a polymerase activity.

25. The method of claim 1 wherein the enzyme having polymerase activity is selected from a DNA polymerase from *Thermus* species, Bacillus species, *Thermococcus* species, *Thermotoga* species, and Pyrococcus species.

26. The method of claim 1 wherein the enzyme having polymerase activity is selected from the group consisting of AmpliTaq Gold® DNA polymerase; AmpliTaq® DNA Polymerase; AmpliTaq® DNA Polymerase, Stoffel fragment; rTth DNA Polymerase; rTth DNA Polymerase XL; Tne, Bst DNA polymerase large fragment from *Bacillus stearothermophilus*; Vent and Vent Exo- from *Thermococcus litoralis*; Tma from *Thermotoga maritima*; Deep Vent and Deep Vent Exo- and Pfu from Pyrococcus; and mutants, variants and derivatives thereof.

27. The method of claim 1 wherein said amplification comprises contacting said nucleobase sequence with an enzyme having a polymerase activity.

28. The method of claim 1 wherein the enzyme having polymerase activity is selected from a DNA polymerase from *Thermus* species, *Bacillus* species, *Thermococcus* species, *Thermotoga* species, and Pyrococcus species.

29. The method of claim 1 wherein the enzyme having polymerase activity is selected from the group consisting of AmpliTaq Gold® DNA polymerase; AmpliTaq® DNA Polymerase; AmpliTaq® DNA Polymerase, Stoffel fragment; rTth DNA Polymerase; rTth DNA Polymerase XL; Tne, Bst DNA polymerase large fragment from *Bacillus stearothermophilus*; Vent and Vent Exo- from *Thermococcus litoralis*; Tma from *Thermotoga maritima*; Deep Vent and Deep Vent Exo- and Pfu from *Pyrococcus*; and mutants, variants and derivatives thereof.

30. A method of amplifying ribosomal DNA in a polymerase chain reaction comprising the steps of:
(a) providing a sample comprising a ribosomal DNA target sequence of interest; and
(b) amplifying at least one nucleobase sequence of said ribosomal DNA to form amplified ribosomal DNA in a mixture of total amplified product;
wherein said amplification is performed in the presence of a sufficient amount of sorbitol and DMSO to reduce non-specific amplification relative to the amount of non-specific amplification observed in the absence of said sorbitol and said DMSO.

31. The method of claim 30 wherein said sorbitol is present in an amount of 0.05 M to 3 M.

32. The method of claim 30 wherein the sorbitol is present in an amount of 0.1 M to 2 M.

33. The method of claim 30 wherein the sorbitol is present in an amount of 0.2 M to 1 M.

34. The method of claim 30 wherein the sorbitol is present in an amount of 0.25 M to 0.5 M.

35. The method of claim 30 wherein said DMSO is present in an amount of 0.5% to 8.0%.

36. The method of claim 30 wherein said DMSO is present in an amount of 1.0% to 6.0%.

37. The method of claim 30 wherein said DMSO is present in an amount of 2.0% to 5.0%.

38. The method of claim 30 wherein said DMSO is present in an amount of 3.0% to 4.0%.

39. The method of claim 30 wherein said DMSO is present in an amount of 1.25% and said sorbitol is present in an amount of 0.15 M.

40. The method of claim 30 wherein said amplification comprises contacting said nucleobase sequence with an enzyme having a polymerase activity.

41. The method of claim 30 wherein the enzyme having polymerase activity is selected from a DNA polymerase from *Thermus* species, *Bacillus* species, *Thermococcus* species, *Thermotoga* species, and Pyrococcus species.

42. The method of claim 30 wherein the enzyme having polymerase activity is selected from the group consisting of AmpliTaq Gold® DNA polymerase; AmpliTaq® DNA Polymerase; AmpliTaq® DNA Polymerase, Stoffel fragment; rTth DNA Polymerase; rTth DNA Polymerase XL; Tne, Bst DNA polymerase large fragment from *Bacillus stearothermophilus*; Vent and Vent Exo- from *Thermococcus litoralis*; Tma from *Thermotoga maritima*; Deep Vent and Deep Vent Exo- and Pfu from Pyrococcus; and mutants, variants and derivatives thereof.

43. A method of detecting bacteria in a sample comprising providing a sample comprising nucleic acid, said nucleic acid comprising at least one ribosomal DNA sequence; and amplifying at least one nucleobase sequence of said nucleic acid, thereby forming an amplified product, wherein said amplification is performed in the presence of an amount of sorbitol and 0.5–8% DMSO effective in reducing non-specific amplification relative to the amount of non-specific amplification observed in the absence of sorbitol and 0.5–8% DMSO.

44. The method of claim 43 wherein said amplification step comprises contacting said nucleic acid sequence with an enzyme having a polymerase activity.

45. The method of claim 44 wherein the enzyme having polymerase activity is selected from a DNA polymerase from *Thermus* species, Bacillus species, *Thermococcus* species, *Thermotoga* species, and Pyrococcus species.

46. The method of claim 44 wherein the enzyme having polymerase activity is selected from the group consisting of AmpliTaq Gold® DNA polymerase; AmpliTaq® DNA Polymerase; AmpliTaq® DNA Polymerase, Stoffel fragment; rTth DNA Polymerase; rTth DNA Polymerase XL; Tne, Bst DNA polymerase large fragment from *Bacillus stearothermophilus*; Vent and Vent Exo- from *Thermococcus litoralis*; Tma from *Thermotoga maritima*; Deep Vent and Deep Vent Exo- and Pfu from Pyrococcus; and mutants, variants and derivatives thereof.

47. The method of claim 43 wherein said amplification step comprises contacting said nucleic acid sequence with an enzyme having a polymerase activity.

48. The method of claim 47 wherein the enzyme having polymerase activity is selected from a DNA polymerase from *Thermus* species, Bacillus species, *Thermococcus* species, *Thermotoga* species, and Pyrococcus species.

49. The method of claim 47 wherein the enzyme having polymerase activity is selected from the group consisting of AmpliTaq Gold® DNA polymerase; AmpliTaq® DNA Polymerase; AmpliTaq® DNA Polymerase, Stoffel fragment; rTth DNA Polymerase; rTth DNA Polymerase XL; Tne, Bst DNA polymerase large fragment from *Bacillus stearothermophilus*; Vent and Vent Exo- from *Thermococcus litoralis*; Tma from *Thermotoga maritima*; Deep Vent and Deep Vent Exo- and Pfu from Pyrococcus; and mutants, variants and derivatives thereof.

50. The method of claim 43 further comprising determining the nucleic acid sequence of said amplified product and comparing said nucleic acid sequence of said amplified product with known bacterial ribosomal DNA sequences.

51. The method of claim 43 further comprising determining the nucleic acid sequence of said amplified product and comparing said nucleic sequence of said amplified product with known bacterial ribosomal DNA sequences.

52. The method of claim 50 wherein said amplified product is purified prior to determining said nucleic acid sequence of said amplified product.

53. The method of claim 51 wherein said amplified product is purified prior to determining said nucleic acid sequence of said amplified product.

54. The method of claim 45 wherein said sample is a clinical sample selected from the group consisting of blood, urine, cerebrospinal fluid, serum, saliva, mucus, skin scraping, gastric secretions and stool.

55. The method of claim 43 wherein said sample is a clinical sample selected from the group consisting of blood, urine, cerebrospinal fluid, serum, saliva, mucus, skin, gastric secretions and stool.

* * * * *